United States Patent [19]

Mendy

[11] Patent Number: 5,405,835
[45] Date of Patent: Apr. 11, 1995

[54] COMPOSITIONS FOR USE IN DIETETICS, REANIMATION AND THERAPEUTICS, CONTAINING A PROTEIN FRACTION BASED ON THREE TYPES OF MINIPEPTIDES

[75] Inventor: Francois Mendy, Boulogne, France

[73] Assignee: Clintec Nutrition Company, Deerfield, Ill.

[21] Appl. No.: 181,662

[22] Filed: Jan. 14, 1994

Related U.S. Application Data

[60] Division of Ser. No. 14,099, Feb. 5, 1993, Pat. No. 5,298,493, which is a continuation of Ser. No. 929,854, Aug. 17, 1992, abandoned, which is a continuation of Ser. No. 809,025, Dec. 16, 1991, abandoned, which is a continuation of Ser. No. 622,408, Dec. 4, 1990, abandoned, which is a continuation of Ser. No. 318,415, Feb. 28, 1989, abandoned, which is a continuation of Ser. No. 909,566, Sep. 22, 1986, abandoned, which is a continuation of Ser. No. 602,493, Apr. 20, 1984, abandoned.

[30] Foreign Application Priority Data

Apr. 20, 1983 [FR] France .................... 83 06444

[51] Int. Cl.⁶ .............................. A61K 37/16
[52] U.S. Cl. ............................ 514/21; 514/18; 514/19; 514/15; 514/16; 514/7; 426/656; 426/657
[58] Field of Search ........... 514/18, 19, 7, 15, 16, 514/21; 426/656, 657

[56] References Cited

U.S. PATENT DOCUMENTS

| | | |
|---|---|---|
| 3,542,560 | 11/1970 | Tomarelli et al. . |
| 3,697,287 | 10/1972 | Winitz . |
| 3,698,912 | 10/1972 | Winitz . |
| 4,216,236 | 8/1980 | Mueller et al. ............. 426/72 |
| 4,282,265 | 8/1981 | Theuer . |
| 4,358,465 | 11/1992 | Brule et al. ............. 426/657 |
| 4,361,587 | 11/1982 | Brule et al. ............. 426/42 |
| 4,427,658 | 1/1984 | Maubois et al. ............. 424/177 |
| 4,462,990 | 7/1984 | Jolles et al. . |
| 5,298,493 | 3/1994 | Mendy ............. 514/21 |

FOREIGN PATENT DOCUMENTS

| | | |
|---|---|---|
| 0022019 | 6/1980 | European Pat. Off. . |
| 0033686 | 1/1981 | European Pat. Off. . |
| 0034083 | 1/1981 | European Pat. Off. . |
| 0049666 | 10/1981 | European Pat. Off. . |
| 0055172 | 12/1981 | European Pat. Off. . |
| 0065663 | 4/1982 | European Pat. Off. . |

OTHER PUBLICATIONS

F. Mendy, *Dietetique Therapeutique et Reanimation Enterale a Faible Debit Continu Conception des Produits,* Inserm, vol. 53, pp. 89, 95 (1975).

West, David W., *A Study of the Enzymic Dephosphorylation of β-Casein and a Derived Phosphoeptide,* Chemical Abstracts, vol. 86, p. 148: 27231p (1977).

*Primary Examiner*—Michael G. Wityshyn
*Assistant Examiner*—C. Sayala
*Attorney, Agent, or Firm*—Hill, Steadman & Simpson

[57] ABSTRACT

A composition intended for use in dietetics, reanimation and therapeutics is provided. The composition includes lactoserum minipeptides, casein minipeptides, and casein minipeptides without phosphopeptides. The selected minipeptides are present in an amount sufficient to assure a proper balance between a level of sulfur-containing amino acids and a level of phosphorus bound to proteins.

20 Claims, No Drawings

COMPOSITIONS FOR USE IN DIETETICS, REANIMATION AND THERAPEUTICS, CONTAINING A PROTEIN FRACTION BASED ON THREE TYPES OF MINIPEPTIDES

This is a division of application Ser. No. 08/014,099, filed Feb. 5, 1993, now U.S. Pat. No. 5,298,493, which is a continuation of Ser. No. 929,854,, filed Aug. 17, 1992, now abandoned, which is a continuation of Ser. No. 809,025, filed Dec. 16, 1991, now abandoned, which is a continuation of Ser. No. 622,408, filed Dec. 4, 1990, now abandoned, which is a continuation of Ser. No. 318,415, filed Feb. 28, 1989, now abandoned, which is a continuation of Ser. No. 909,566, filed Sep. 22, 1986, now abandoned, which is a continuation of Ser. No. 602,493, filed Apr. 20, 1984, now abandoned.

The present invention describes new compositions intended for use in dietetics, reanimation and therapeutics, which compositions contain a protein fraction based on three types of minipeptides. The present invention also comprises methods of using these compositions. The compositions of the present invention contain glucides, vitamins, mineral salts, a lipid fraction and a protein fraction. The protein fraction is characterized in that it contains the following three types of minipeptides:
lactoserum minipeptides,
total casein minipeptides,
casein minipeptides without phosphopeptide.

The lactoserum minipeptides may be obtained by total enzyme hydrolysis of lactoserum proteins. This enzyme hydrolysis process and the minipeptides obtained by this process are described in the U.S. patent published under U.S. Pat. No. 4,427,658.

The two other types of minipeptides contained in the protein fraction of the compositions of the invention may be prepared starting with phosphocaseinates of monovalent or bivalent cations, treated according to the processes described in the two U.S. patents published under U.S. Pat. Nos. 4,361,587 and 4,358,465.

These two patents indicate, firstly, how the total casein minipeptides are obtained by enzyme hydrolysis of the phosphocaseinates of monovalent or bivalent cations. Then, these two patents describe the different stages which enable, for the one part phosphopeptides and for the other part minipeptides without phosphopeptides to be separated, starting with total casein minipeptides.

Numerous products based on minipeptides used in dietetics or therapeutics and more particularly, in therapeutic nutrition, are already on the market. These products possess a protein fraction containing, in variable proportions, free amino acids and minipeptides with more or less long chains. A few years ago, only products based on amino acids were available but more and more, products based on small peptides are now preferred. In fact, the products based on amino acids are always hyper-osmolar, and thus, often lead to digestive intolerances. Clinical research, like for example, that of SILK D., PERRETT D., CLARK M., "Intestinal transport of two dipeptides containing the same two neutral amino acids in man", Clin. Sci. Mol. Med 45: 291-299, 1973, showed, moreover, the improved absorption of small peptides compared with free amino acids.

The first advantage of the compositions according to the invention is that they contain a protein fraction which only has minipeptides and is practically deprived of free amino acids (present in a proportion of less than 15%).

In addition, the works of KEOHANE P., BROWN Barbara, GRIMBLE G., SILK D., "The peptide nitrogen source of elemental diets—comparisons of absorptive properties of five partial enzymic hydrolysates of whole protein", A.S.P.E.N. 6th Clinical Congress, 3-6 Feb. 1982, San Francisco, showed the improved absorption of small peptides when the latter result from a mixture containing, among others, casein peptides and lactoserum peptides, as compared with peptides of other origin.

The compositions according to the invention display a second advantage of combining minipeptides, which by their nature, are very well absorbed by the organism.

However, a protein mixture based on casein minipeptides and lactoserum minipeptides in a composition intended for dietetics, reanimation or therapeutics would cause:
either a too high level of sulphur-containing amino acids, if the lactoserum peptides were present in too high a quantity;
or a too high level of phosphorus bound up to proteins if on the other hand the casein minipeptides were in too high a quantity.

It was therefore necessary to produce a mixture of casein minipeptides and lactoserum minipeptides for the one part, respecting the necessary balance between these two types of minipeptides and, for the other part, ensuring adequate levels of organic phosphorus bound to proteins and amino acids containing sulphur.

Only casein minipeptides bring in phosphorus bound to proteins; lactoserum minipeptides do not contain any. The necessity for a balance between casein minipeptides and lactoserum minipeptides leads to an excessive contribution of phosphorus bound to proteins.

It was therefore useful to produce compositions according to the invention in which a part of the total casein minipeptides was replaced by minipeptides without phosphopeptide so as to diminish the level of phosphorus bound to proteins resulting from the casein in these compositions.

In this way, the content of phosphorus bound to proteins is therefore readjusted and at the same time, the content of sulphur-containing amino acids is regulated to the desired level.

Moreover, the $H^{\oplus}$ ions load depends from the contribution of sulphur-containing amino acids and the contribution of phosphorus bound to proteins. This is an important parameter in invalids for whom the compositions of the invention are intended. These patients very often have illnesses of insufficiency of kidney function, with a deficiency of regulating the acid-base balance. The adjustment of the level of organic phosphorus in the compositions according to the invention therefore also enables, more generally, the variation of the $H^{\oplus}$ ions load of the compositions. The present invention therefore produces compositions in which the associated three types of minipeptides enable the variation of the level of phosphorus bound to proteins.

The level of phosphorus bound to proteins thus obtained in these compositions is variable and depends on the proportion of the phosphoprotein part contained in these compositions. In order to obtain a physiological level of organic phosphorus, the phosphoprotein fraction must represent, preferably, from 1% to 10% by weight of the compositions of the invention.

These preceeding conditions notably enable the realization of a combination of the three types of minipeptides. This leads to compositions in which the level of phosphorus bound to proteins is at least equal to that present in human milk, that is to say in the order of 1.5 mg per g of protein and at most is equal to that present in cows' milk, that is to say in the order of 6.6 mg per g of protein.

The present invention therefore has notably as its subject compositions characterized in that the weight of the protein fraction represents 1% to 10% of the total weight, and further characterized in that the level of phosphorus bound to proteins is between 1.5 mg per g of protein and 6.6 mg per g of protein.

Furthermore, according to the respective quantities of the three types of minipeptides; the distribution in amino acids of the compositions of the invention is variable. Thus, the three types of associated minipeptides enable different amino-grams to be obtained which may be adapted to specific pathological situations.

The combination of the three types of minipeptides, especially in approximately equal quantities, in the protein fraction of the compositions according to the invention, enables a distribution in amino acids to be available, thus ensuring a maximal nutritional efficiency. The present invention therefore includes compositions characterized in that the three types of minipeptides are present in approximately equivalent quantities by weight. In these conditions, the level of phosphorus bound to proteins is about 3 mg/g of protein.

The invention therefore includes compositions characterized in that the level of phosphorus bound to proteins is about 3 mg/g of protein and in particular, compositions characterized in that the distribution of amino acids of the protein fraction is that given below, the following figures being expressed in grams of amino acid per 100 g of amino acids:

| | |
|---|---|
| Ile | 5.1 |
| Leu | 10.1 |
| Lys | 8.5 |
| Met | 2.3 |
| Cys | 1.6 |
| Phe | 4.6 |
| Tyr | 4.9 |
| Thr | 4.4 |
| Trp | 1.8 |
| Val | 5.9 |
| Arg | 3.3 |
| His | 2.5 |
| Ala | 3.6 |
| Asp | 8.4 |
| Glu | 15.9 |
| Gly | 1.8 |
| Pro | 8.4 |
| Ser | 4.7 |

This aminogram thus enables an increase in the ratio of branched amino acids, while retaining a high level of lysin.

It is to be understood that the compositions of the invention provide all the necessary nutritive elements, as well as protein elements, in intended proportions. They also contain glucides, ensuring 50% to 60% of the total energy contribution (=T.E.C.), and vitamins (A, D, E, C, $B_1$, $B_2$, PP, $B_6$, $B_{12}$, folic acid, biotin, $B_5$, $K_1$, choline).

The compositions according to the invention also ensure that the physiological needs in mineral elements are met. They also contain a lipid fraction ensuring 30%–35% of the T.E.C.

The invention includes compositions characterized in that their lipid fraction has approximately the following composition:

| | |
|---|---|
| medium chain triglycerides | 56.4% |
| Oenothera oil | 25.6% |
| soya oil | 18% |

More than half of this lipid fraction is composed of short or medium chain triglycerides. This enables a good tolerance, even in invalids suffering from malabsorption or maldigestion of lipids or from a bad metabolization of essential fatty acids. In fact, the short or medium chain triglycerides are easily assimilable by the organism, even when digestion is disturbed.

This lipid fraction ensures the contribution of the following essential fatty acids:
- linoleic acid (=9.6% of the T.E.C.)
- γ-linoleic acid (=0.8% of the T.E.C.)
- α-linoleic acid (=0.4% of the T.E.C.).

The acids named above or their usual higher polyunsaturated derivatives may be specifically added. This addition may be carried out by adding synthesized triglycerides of two types:
- synthesized triglycerides in position 1, 2 or of linoleic or γ-linoleic acid (C18:3,ω6), of dihomo-α-linoleic acid (C20:3,ω6), of arachidonic acid (C20:4,ω6), of docosatetraenoic acid (C22:4,ω6), or of docosapentaenoic acid (C22:5,ω6);
- synthesized triglycerides in position 1, 2 or 3 of α-linoleic acid (C18:3,ω3), of eicosatetraenoic acid (C20:4,ω3), of eicosapentaenoic acid (C20:5,ω3), of docosahexaenoic acid (C22:6,ω3) or of docosapentaenoic acid (C22:5,ω3).

The compositions of the invention are useful in dietetics, reanimation and therapeutics.

The application therefore also has as its subject the application of the compositions as previously defined as food or food supplements, meeting specific nutritional needs.

The compositions of the invention are useful when a post-operative nutritional assistance is necessary. They are also usable in pre-operative nutrition, in particular when a residue free diet is desired. In fact, the compositions of the invention are completely absorbed in the proximal part of the small intestine, leaving only a minimal faecal residue.

The compositions of the invention may also be used in the case of disorders in the alimentary canal, and notably when the intestinal surface is reduced or displays disease. This is the case for example with ailments characterized by a chronic inflammation associated with fistulae, or by absorption trouble caused by a reduction of the surface of the small intestine. It is also the case with Crohn's disease, and chronic intestinal diseases.

The compositions of the invention also find use when troubles with digestive secretion lead to poor digestion or malabsorption as in:
- acute pancreatitis,
- malabsorption syndrome caused by a malignant reticulosis,
- certain diseases of the system,
- ischemic trouble of the intestine.

Furthermore, each time that there is an inflammatory attack in the intestine there exists a risk of allergy to whole proteins. The compositions of the invention may therefore also be used to avoid the occurrence of allergies in the course of inflammatory diseases of the intestine.

The invention therefore also includes food or food supplements as well as therapeutic nutrition products containing the compositions as previously defined, possibly combined with a neutral vehicle suitable for oral or enteral administration.

The present invention also includes the application as medicaments of the compositions, as previously defined. The new compositions of the invention constitute, because of their properties, very useful medicaments in the treatment of the ailments described above. The usual dose of the compositions of the invention varies depending on the condition of the patient, the ailment in question and the administration route chosen.

For example, a dose of the composition of the invention may be administered ensuring a protein contribution of about 47 g to 118 g and preferably, of about 71 g, a lipid contribution of about 58.5 g to 146 g and preferably, of about 88 g, a glucide contribution of about 197 g to 493 g and preferably of about 296 g, it being understood that these doses are per day and by oral route in an adult human.

The present invention also includes pharmaceutical compositions containing one of the above medicaments, possibly combined with a usual neutral vehicle, suitable for oral or enteral administration. These pharmaceutical preparations may be presented in the forms currently utilized in human medicine, either in liquid form or in the form of a powder, and are contained, for example, in metal boxes, flasks, bags or plastic bottles.

In the preparations given below in the examples, 1–5 g of maltodextrin may be replaced by galactose.

The examples given below illustrate the invention without, however, limiting it.

EXAMPLE 1

A liquid dietetic preparation was prepared for oral or enteral use, with the following formula:
Centesimal composition
- glucides : 13.15 g (maltodextrins)
- lipids : 3.9 g
of which:

| Medium-chain triglycerides | 2.2 g |
| Oenothera oil | 1.0 g |
| soya oil | 0.7 g |

- proteins : 3.15 g
of which:

| lactoserum minipeptides | 1.05 g |
| total casein minipeptides | 1.05 g |
| casein minipeptides without phosphopeptide | 1.05 g |

- vitamins : according to the American norms of RDA and ESADDI A, D, E, C, $B_1$, $B_2$, PP, $B_6$, $B_{12}$, folic acid, biotin, $B_5$, $K_1$, choline;
- minerals : according to the American norms of RDA and ESADDI

| calcium, phosphorus, magnesium, iron, zinc, iodine, sodium, potassium, chloride, copper, manganese, selenium | 0.404 g |
| vehicle q.s. for | 100 ml. |

- R.D.A. : "Recommended Dietary Allowances" 9th edition 1980 Committee on Dietary Allowances, Food and Nutrition Board Division of Biological Sciences, National Research Council, National Academy of Sciences, Washington, D.C., 1980
- E.S.A.D.D.I. : "Estimated Safe and Adequate Daily Dietary Intakes" (Nutrition Reviews, Vol. 38, No. 8 Aug. 1980, p 291) (Journal of The American Dietetic Association, Vol 76, No. 3, Mar. 1980).

For information only, the lipid fraction of this preparation ensures the following contribution of essential fatty acids:
- linoleic acid: 1.1 g
- γ-linoleic acid: 0.08 g
- α-linoleic acid: 0.04 g.

EXAMPLE 2

A liquid dietetic preparation for oral or enteral use was prepared, with the following formula:
Centesimal composition
- glucides 15.6 g (Maltodextrins)
- lipids 5.2g
of which:

| medium-chain triglycerides | 2.9 g |
| Oenothera oil | 1.2 g |
| soya oil | 1.05 g |
| lecithin | 0.05 g |

- proteins : 6 g
of which:

| lactoserum minipeptides | 2 g |
| total casein minipeptides | 2 g |
| casein minipeptides without phosphopeptides | 2 g |

- vitamins : according to the American norms of RDA and ESADDI A, E, C, $B_1$, $B_2$, PP, $B_6$, $B_{12}$, folic acid, biotin, $B_5$, choline
- minerals : according to the American norms of RDA and ESADDI

| calcium, phosphorus, magnesium, sodium, potassium, ion chloride, iron, zinc, copper, manganese, iodine, selenium | 0.562 g |
| vehicle q.s. for | 100 ml. |

The preparation of 7500 litres of the composition of example 1 (the 7500 litres were then separated into metal tins ) , is carried out in 3 stages as follows:

1st stage: Preparation of a lipid emulsion

The material used is the following:
- 2×2000 litres stainless steel tanks, equipped with:
  * an agitation system
  * a heating and cooling system
  * a vacuum apparatus
  * a centrifugal pump
  * a high pressure pump 1500 litres of osmosis-treated water is introduced into one 2000 litre tank then heated under agitation. When the temperature reaches 65° C. the following are added:

- 75 kg of Onarge oil
- 37 kg 500 of soya lecithin
- 97 kg 500 of medium-chain triglycerides
- 37 kg 500 of glycerol monostearate.

Agitation is continued and after starting the cooling of the mixture, vitamins E, A and D (previously dissolved in 48 kg 750 of soya oil) are added.

When the temperature is about 20° C., the first transfer is started by the high pressure pump.

The pressure is adjusted to 50 kg/cm$^2$ at the second stage of the pump and to 250 kg/cm$^2$ at the first.

At the outlet, the product is collected in the second tank.

One proceeds in this way with 4 transfers by the high pressure pump, passing alternatively from one tank to the other.

A rapid check of the size of the Liposomes of the emulsions may be carried out with the Coulter Counter.

2nd stage : Preparation of a starch phase
The material used is the following:
- an 8000 litre stainless steel tank equipped with:
  * a mechanism for agitation
  * a vacuum apparatus
- a 500 litre stainless steel tank equipped with:
  * a mixing turbine
- a plate exchanger provided with 3 circuits:
  * one for heating
  * one for cooling to 15° C.
  * one for cooling to 5° C.
- 2 centrifugal pumps of 20m$^3$/hour. The mixer being in a closed circuit with the tank, the pumps and the exchanger, 3700 litres of osmosis-treated water are added and heated to 85° C.

When this temperature is reached, 195 kg of dehydrated starch (1 to 4% according to the viscosity desired) is added by the mixer and the temperature is kept at 85° C. for 30 minutes.

At the end of this period, the temperature is lowered to 50° C. by means of the cooling section of the exchanger then the following are added successively:
- 98 kg of lactoserum minipeptides,
- 92 kg of total casein minipeptides,
- 100 kg 500 of casein minipeptides without phosphopeptides,
- 850 kg of maltodextrin. The temperature is lowered to 40° C. and the following are introduced:
- magnesium chloride,
- potassium hydrogen phosphate,
- calcium chloride,
- sodium chloride,
- choline chloride,
- potassium iodide and sodium selenite. The temperature of the mixture is lowered to 25° C. and the following are added:
- ascorbic acid,
- iron sulphate
- nicotinamide or vitamin PP,
- zinc citrate,
- calcium pantothenate,
- manganese sulphate,
- pyridoxine hydrochloride or vitamin B$_6$,
- thiamin hydrochloride or vitamin B$_1$,
- copper sulphate,
- vitamin B$_{12}$ 1% on mannitol,
- riboflavine or vitamin B$_2$,
- folic acid,
- biotin.

3rd stage : preparation of the final mixture

Whilst the starch phase is under agitation in the 8000 litre tank, the lipid emulsion prepared in the first stage is introduced by means of a centrifugal pump. After adjusting the level of the tank to 7450 litres with osmosis-treated water and the pH to 7.10 by means of a potassium hydroxide solution, checking the level of the tank and measuring the dry material contents in the tank, the final vacuum is made and nitrogen is added to the tank.

The final mixture obtained in this way is then sterilized by filtration then, at 150° C. for 8 seconds by a passage in a coil circuit.

The final product is then distributed between 375 ml. metal boxes; the latter being closed aseptically (the boxes and lids are previously sterilized by superheated steam).

Clinical study of the product of example 1

6 invalids, from 15 to 53 years in age were observed over a period of 14 days in the course of gastro-enterological reanimation. These people displayed serious gastrointestinal disorders with one or more complications (for example: acute chlolecystitis with oedematous pancreatitis; bullet wound leading to duodenal injury, an injury of the liver, an injury of the straight colon, acute pancreatitis with toxi-infectious syndrome).

The aim of this study was threefold:
1) To study the tolerance of the product;
2) To evaluate the absorption; and
3) Assess the nutritional impact of the product.

Throughout the duration of this study, the six patients received food by enteral route only through a feeding tube with a continuous flow, 24 hours out of 24.

This food was composed exclusively of the product of example 1 for all the patients, except for one for whom an addition of rice water had been made because of a severe toxi-infectious syndrome.

The following table indicates, for each patent:
- the energy contribution per 24h in Kcal,
- the volume of the product of example 1 administered per 24 hours,
- the daily contribution in nitrogen (g/24h.) corresponding to the administration of nutritional support.

|  | Patient | | | | | |
| --- | --- | --- | --- | --- | --- | --- |
|  | 1 | 2 | 3 | 4 | 5 | 6 |
| Energy contribution Kcal/24 h. | 4125 | 4125 | 4125 | 2300 | 3750 | 3750 |
| Volume of product of example 1 in ml. per 24 h. | 4125 (11 × 375 ml. boxes) | 4125 | 4125 | 2250 (6 × 375 ml. boxes) | 3750 (10 × 375 ml. boxes) | 3750 |
| Nitrogen contribution g/24 h. | 22 | 22 | 22 | 12 | 20 | 20 |

1) Study of the tolerance of the product
The following have been used as criteria of tolerance:
- acceptability,
- vomitting,
- abdominal pains,
- diarrhoea,
- flatulence.

According to these criteria, with a daily intake of 3750 to 4125 ml. of product, the patients 1, 2, 3, 5 and 6 displayed an excellent tolerance.

For patient 4, the criteria of tolerance defined above were also good, with a reduction in the intake to 2250 ml/day of the product.

2) Study of the absorption and the nutritional efficiency

The nutritional value of the product of example 1 was studied by means of the following results (see table I):

- The coefficient of absorption of minipeptides of the product of example 1, even in the case of severe gastro-enterological disorders and a toxi-infection, was greater than 95% in all but one case. Moreover, in this group of patients suffering from severe gastro-enterological problems which, in certain instances, makes any enteral nutrition impossible, the coefficient of absorption is distinctly greater than the average coefficient of absorption of the usual patients under treatment.

Thus, even with a nitrogen and calorie intake clearly reduced, the efficiency of the product enabled the maintenance of a positive nitrogen balance.

- Albumin: one of the principal criteria of protein metabolism is the level of plasma albumin. The level of albumin increased significantly in the course of treatment.

Likewise, weight increase rose significantly (2.5 kg)

In this study, all the other metabolic parameters remained identical or increased within normal limits, or improved.

Finally, the clinical development is excellent for the 6 patients.

The nutritional criteria and the clinical condition are thus improved in a similar way to the nitrogen balance.

TABLE I

| PATIENT | AGE | COEFFICIENT OF ABSORPTION OF MINI-PEPTIDES (N) | ALBUMIN D0 | ALBUMIN D14 | WEIGHT D0 | WEIGHT D14 | OTHER METABOLIC PARAMETERS | CLINICAL RESULTS |
|---|---|---|---|---|---|---|---|---|
| 1. | 52 | 96.5% | 31 | 33.4 | 60 | 60 | All the parameters remained the same or rose within the normal limits or improved. The nitrogen balance was positive from the 2nd day. | Excellent progess with recovery |
| 2. | 51 | 98.1% | 30.8 | 39 | 71 | 75 | All the parameters remained the same or rose within the normal limits or improved. The nitrogen balance was positive from the 2nd day. | Excellent progress with recovery |
| 3. | 47 | 98.7% | 36.5 | 43.7 | 70 | 72 | All the parameters remained the same or rose within the normal limits or improved. The nitrogen balance was positive from the 2nd day. | Excellent progress with recovery |
| 4. | 44 | 95.5% | 38 | 45.9 | 64 | 58 | All the parameters remained the same or rose within the normal limits or improved. The nitrogen balance was positive from the 2nd day. | Serious toxi-infection controlled + recovery |
| 5. | 15 | 86.5% | 33 | 43.6 | 43 | 45 | All the parameters remained the same or rose within the normal limits or improved. The nitrogen balance was positive from the 2nd day. | Excellent progress with recovery |
| 6. | 16 | 97.5% | 41 | 48 | 68 | 70 | All the parameters remained the same or rose within the normal limits or improved. The nitrogen balance was positive from the 2nd day. | Excellent progress with recovery |

- The nitrogen balance appears positive from the second day, varying between +9.25 and +15g/24h, except for patient 4 (+3g). This patient has a toxi-infection necessitating a reduction in intake (12 g of nitrogen/24 hours).

Conclusion

The product of example 1, utilized in this clinical test on patients displaying severe gastro-intestinal disorders with one or more complications, displays an excellent nutritional efficiency which enables the following to be ensured:
- a stabilization or improvement of the biological parameters within the normal limits;
- a coefficient of absorption of minipeptides greater than 95%;
- a clear, positive nitrogen balance;
- an improvement in the clinical condition.

Furthermore, this product displays a very good tolerance.

I claim:

1. A composition comprising:
lactoserum minipeptides,
casein minipeptides, and
casein minipeptides without phosphopeptides, wherein the lactoserum minipeptides, the casein minipeptides, and the casein minipeptides without phosphopeptides are present in amount sufficient to assure physiological levels of sulfur-containing amino acids and phosphorus bound to proteins.

2. The composition of claim 1 wherein the lactoserum minipeptides, casein minipeptides and casein minipeptides without phosphopeptides are present in substantially equivalent quantities by weight.

3. The composition of claim 1 further comprising glucides, vitamins, mineral salts, and lipids.

4. The composition of claim 1 further comprising a lipid fraction that comprises medium chain triglycerides, oenothera oil, and soya oil.

5. The composition of claim 4 wherein the lipid fraction is further defined by having the following approximate composition: medium chain triglycerides (56.4%); oenothera oil (25.6%); and soya oil (18.0%).

6. The composition of claim 1 wherein the lactoserum minipeptides, casein minipeptides, and casein minipeptides without phosphopeptides comprise 1 to 10% of the total weight of the composition.

7. The composition of claim 1 wherein the level of phosphorus bound to proteins is between approximately 1.5 mg/g to about 6.6 mg/g of protein.

8. The composition of claim 1 wherein the level of phosphorus bound to proteins is approximately 3 mg/g of protein.

9. The composition of claim 1 further comprising an amino acid distribution as follows, the following figures being expressed in grams of amino acid per 100 g of amino acids:

| | |
|---|---|
| Ile | 5.1 |
| Leu | 10.1 |
| Lys | 8.5 |
| Met | 2.3 |
| Cys | 1.6 |
| Phe | 4.6 |
| Tyr | 4.9 |
| Thr | 4.4 |
| Trp | 1.8 |
| Val | 5.9 |
| Arg | 3.3 |
| His | 2.5 |
| Ala | 3.6 |
| Asp | 8.4 |
| Glu | 15.9 |
| Gly | 1.8 |
| Pro | 8.4 |
| Ser | 4.7. |

10. A composition comprising:
lactoserum minipeptides,
casein minipeptides, and
casein minipeptides without phosphopeptides, wherein the lactoserum minipeptides, casein minipeptides and casein minipeptides without phosphopeptides are present in substantially equivalent quantities by weight.

11. The composition of claim 10 further comprising glucides, vitamins, mineral salts, and lipids.

12. The composition of claim 10 further comprising a lipid fraction that comprises medium chain triglycerides, oenothera oil, and soya oil.

13. The composition of claim 10 wherein the lactoserum minipeptides, casein minipeptides, and casein minipeptides without phosphopeptides comprise 1 to 10% of the total weight of the composition.

14. The composition of claim 10 wherein the level of phosphorus bound to proteins is between approximately 1.5 mg/g to about 6.6 mg/g of protein.

15. The composition of claim 10 further comprising an amino acid distribution as follows, the following figures being expressed in grams of amino acid per 100 g of amino acids:

| | |
|---|---|
| Ile | 5.1 |
| Leu | 10.1 |
| Lys | 8.5 |
| Met | 2.3 |
| Cys | 1.6 |
| Phe | 4.6 |
| Tyr | 4.9 |
| Thr | 4.4 |
| Trp | 1.8 |
| Val | 5.9 |
| Arg | 3.3 |
| His | 2.5 |
| Ala | 3.6 |
| Asp | 8.4 |
| Glu | 15.9 |
| Gly | 1.8 |
| Pro | 8.4 |
| Ser | 4.7. |

16. A composition comprising:
a lipid source;
a vitamin source; and
lactoserum minipeptides, casein minipeptides, and casein minipeptides without phosphopeptides, wherein the lactoserum minipeptides, the casein minipeptides, and the casein minipeptides without phosphopeptides are present in amounts sufficient to assure physiological levels of sulfur-containing amino acids and a level of phosphorus bound to proteins.

17. The composition of claim 16 wherein the lactorserum minipeptides, casein minipeptides and casein minipeptides without phosphopeptides are present in substantially equivalent quantities by weight.

18. The composition of claim 16 further comprising a lipid fraction that comprises medium chain triglycerides, oenothera oil, and soya oil.

19. The composition of claim 16 wherein the lactoserum minipeptides, casein minipeptides, and casein minipeptides without phosphopeptides comprise 1 to 10% of the total weight of the composition.

20. The composition of claim 16 further comprising amino acid distribution as follows, the following figures being expressed in grams of amino acid per 100 g of amino acids:

| | |
|---|---|
| Ile | 5.1 |

| -continued | |
|---|---|
| Leu | 10.1 |
| Lys | 8.5 |
| Met | 2.3 |
| Cys | 1.6 |
| Phe | 4.6 |
| Tyr | 4.9 |
| Thr | 4.4 |
| Trp | 1.8 |

| -continued | |
|---|---|
| Val | 5.9 |
| Arg | 3.3 |
| His | 2.5 |
| Ala | 3.6 |
| Asp | 8.4 |
| Glu | 15.9 |
| Gly | 1.8 |
| Pro | 8.4 |
| Ser | 4.7. |

* * * * *